United States Patent [19]

Pellenbarg et al.

[11] Patent Number: 4,886,358
[45] Date of Patent: Dec. 12, 1989

[54] ORGANIC VAPOR ASSAY BY RAMAN SPECTROSCOPY

[75] Inventors: Robert E. Pellenbarg, Silver Spring, Md.; David E. Tevault, Springfield, Va.

[73] Assignee: The United States of America as represented by the Secretary of the Navy, Washington, D.C.

[21] Appl. No.: 200,324

[22] Filed: May 31, 1988

[51] Int. Cl.$^4$ .................. G01J 3/44; G01N 21/65
[52] U.S. Cl. ........................ 356/301; 356/36
[58] Field of Search ............... 356/36, 38, 301

[56] References Cited

U.S. PATENT DOCUMENTS

| | | | |
|---|---|---|---|
| 2,370,703 | 3/1945 | Zaikowsky | 62/175 |
| 2,512,040 | 6/1950 | Slobod | 62/175.5 |
| 2,527,121 | 10/1950 | Dudenbostel, Jr. et al. | 356/301 |
| 2,527,122 | 10/1950 | Heigl et al. | 356/301 |
| 3,650,696 | 3/1972 | Eads | 23/230 |
| 3,723,007 | 3/1973 | Leonard | 356/301 |
| 3,746,513 | 7/1973 | Warnick et al. | 23/232 |
| 3,759,617 | 9/1973 | Barringer | 356/36 |
| 3,906,241 | 9/1975 | Thompson | 250/574 |
| 4,023,398 | 5/1977 | French et al. | 73/23 |
| 4,071,298 | 1/1978 | Falconer | 356/73 |
| 4,158,772 | 6/1979 | Reedy | 356/301 |
| 4,620,284 | 10/1986 | Schnell et al. | 364/498 |

OTHER PUBLICATIONS

Atmospheric Transport of DMMP Vapors as Monitored by Raman Spectroscopy—D. E. Tevault, K. Fujii, R. E. Pellenbarg, Proceedings of the 1986 U.S. Army Chemical Research, Development and Engineering Center Scientific Conference on Chemical Defense Research, 18–21 Nov. 1986, vol. 2, published Jun. 1987, pp. 725–729.
Raman Spectroscopy of Chemical Agents Simulants—S. D. Christesen and M. H. Heyl, Proceedings of the 1985 Scientific Conference on Chemical Defense Research, published Apr. 1986, pp. 707–712.
Matrix Isolation Microsampling Procedures in Quantitative Fourier Transform Infrared Spectrometry—D. M. Hembree, E. R. Hinton, Jr., R. R. Kemmerer, G. Mamnantov and E. L. Wehry, Applied Spectroscopy, vol. 33, No. 5, (1979), pp. 477–480.
Raman Spectroscopy—D. L. Gerrard and H. J. Bowley, Anal. Chem. (1986), vol. 58, No. 5, pp. 6R–13R.
The Use of Lasers in Raman Spectroscopy—D. L. Gerrard, Anal. Proce., vol. 22, No. 4, Apr. 1985, pp. 115–116.

Primary Examiner—F. L. Evans
Attorney, Agent, or Firm—Thomas E. McDonnell; Jimmy Wheelington

[57] ABSTRACT

A method of and apparatus for analyzing for low concentrations of organic material in the atmosphere without the removal of water wherein an air sample is collected and cooled to form a condensate consisting essentially of water and organic material. The condensate is analyzed by Raman spectroscopy to detect and quantify the organic material.

21 Claims, 4 Drawing Sheets

ORGANIC VAPOR ASSAY BY RAMAN SPECTROSCOPY

BACKGROUND OF THE INVENTION

1. Field of the Invention

This invention relates to an analytical method and device for atmospheric analysis and, more specifically, to a method and device for detecting low concentrations of organophosphorus material in the atmosphere.

2. Description of the Prior Art

Environmental chemistry has been concerned with detection and measurement of organic material in the atmosphere or aqueous solutions. Techniques such as gas chromatography, infrared spectroscopy and chemically sensitive electronic devices have been applied (*Process Instruments and Controls Handbook*– Considine, P. 6-1-6-213 ). Water acts as an interferant in each of these analytical methods; therefore, it is necessary to remove the water before analysis can be done (*Identification & Analysis of Organic Pollutants in Water*-Keith, p.113; *Modern Practice of Gas Chromatography* — Grob, p.135). It is advantageous to use an analytical method for organic material which does not require removal of water.

The Raman spectrometer detector has been used to analyze organic material in the presence of water. The Raman spectra results from scattering of source light directed on the sample at an angle. Water is transparent to laser light used in Raman spectroscopy since it exhibits very weak Raman scattering and, therefore, is a good solvent for material to be analyzed by Raman spectroscopy. In addition, since the Raman effect is exhibited most strongly by nonpolar homoatomic groups, such as carbon-carbon bonds, aqueous solutions of organic compounds are good candidates for Raman spectroscopic analysis as shown in FIG. 1.

Prior art describes uses of Raman spectroscopy for atmospheric and chemical analysis but does not include condensation as a method to concentrate low quantity components for analysis. Schnell (U.S. Pat. No. 4,620,284) teaches comparison of the digitized spectra of an unknown to reference spectra by means of a computer. Leonard (U.S. Pat. No. 3,723,007) teaches remote quantitative atmospheric analysis by subjecting the atmosphere to pulse laser radiation to determine distance and composition from the Raman scatter. Falconer (U.S. Pat. No. 4,071,298) teaches detection of the presence and the nominal size of aerosol particles by Rayleigh (unshifted) scattered light and their composition and mass by Raman and fluorescent (shifted) scattered light. Dudenbostel (U.S. Pat. Nos. 2,527,121; 2,527,122) teaches determination of the percentage of aromatics ("121") and olefins ("122") in a hydrocarbon mixture by determining the presence and strength of a spectra within a certain wavelength. However, sample preparation has not been a significant factor since detection of low concentrations was not an objective.

One drawback in the use of Raman spectroscopy is the weak spectra generated. Use of a laser can strengthen the spectra but for a sample in which the concentration of the material for which the analysis is being done is small, the problem still exists. Thompson (U.S. Pat. No. 3,906,241) addressed this problem by designing a sample container which, by means of fiberoptics, passes the light beam through the sample several times to strengthen the spectra. Leonard (U.S. Pat. No. 3,723,007) used photomultipliers to strengthen the signal.

Cold trap technology has been applied to gas concentration. Slobod (U.S. Pat. No. 2,512,040) teaches gas separation by cooling a gas mixture with liquid nitrogen to recover gaseous hydrocarbons by freezing them out of the noncondensable gases. Zaikowsky (U.S. Pat. No. 2,370,703) teaches preparation of samples for analysis by separating a gas mixture into gas and liquid components by collecting the gas and condensate in successive stages of freezing and revaporizing. However, the prior art does not suggest a method and device for screening the atmosphere for low concentrations of organic compounds in the range of 1 to 500 parts per billion.

The detection of low concentrations of organophosphorus compounds has application in the analysis of industrial and agricultural wastes and chemical warfare agents. Even at low concentrations, these compounds can be toxic. It has been demonstrated that detection of an organophosphorus compound, such as dimethylmethylphosphonate (DMMP), is possible with Raman spectroscopy ("Raman Spectroscopy of Chemical Agents and Simulants"—Christesen, Heyl, *Proceedings of the* 1985 *Scientific Conference on Chemical Defense Research*, p.707.) The problem has been to detect concentration as low as 1-500 parts per billion.

SUMMARY OF THE INVENTION

Accordingly, one object of this invention is to provide a method to analyze for low concentrations of organic material in the atmosphere without removal of water and an apparatus for practicing that method.

Another object of this invention is to provide a method to detect and quantify low concentrations of organophosphorus compounds and an apparatus for practicing that method.

These and other objects are accomplished by a method for collecting an air sample, cooling the air sample to form a condensate consisting essentially of water and organic material and analyzing the condensate by Raman spectroscopy to detect and quantify the organic material and an apparatus for practicing that method.

BRIEF DESCRIPTION OF THE DRAWINGS

The invention may be better understood by reference to following drawings.

DESCRIPTION OF THE PREFERRED EMBODIMENT

This invention provides a method of concentrating the organic vapor in an air sample by condensing the organic material and the water vapor without condensing the other atmospheric gases to form a concentrated sample which can be analyzed by Raman spectroscopy. It can be used to analyze a sample of low concentration organic material by Raman spectroscopy without subjecting the sample to multiple passes of the light source beam.

Figure 2:
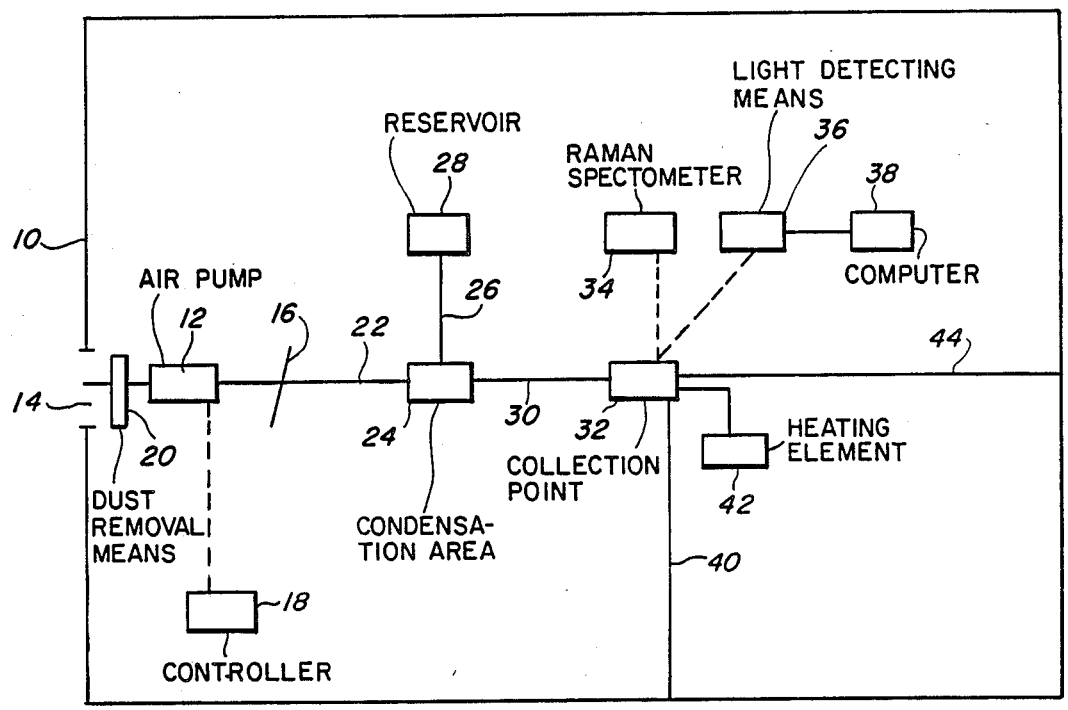
FIG. 2 is a schematic of the general embodiment of the invention.

Referring now to the drawings, and more particularly to FIG. 2 thereof, which illustrates a general embodiment of this invention in which a housing 10 contains an air pump 12 of any known type used for collecting an air sample from the atmosphere in a continuous or noncontinuous manner draws air into the apparatus through an opening 14. In noncontinuous operation the air flow is controlled by any known means to control air flow such as a movable shutter valve 16 or deactivation of the air pump 12 by means of a control 18.

In some situations it is advantageous to remove dust and other particulate matter from the air flow. This can be accomplished by any known means to remove dust and other particulate matter from air, such as a filter or particle ionization device 20 located inside the opening 14 in the housing 10.

After the air pump 12 draws the air sample through the opening 14 in the housing, the air sample passes into conduit 22, which is any of the usual conduits used to transfer air. The conduit 22 channels the air sample to a condensation area 24 within the housing 10 where the air sample is cooled until a condensate consisting essentially of organic material and water is formed.

Condensation is by any known refrigeration means, including a mechanism in which a coil around the conduit 22 transferring the air sample contains any of the known types of refrigerant used to cool to a temperature in the range from the cryogenic temperature of liquid air to the freezing point of water to form a condensate consisting essentially of organic material and water. As illustrated in FIG. 2, sufficient distilled water to liquefy the condensate is added through conduit 26 from reservoir 28 to form a liquid solution of water and organic material. The liquid solution is transferred by conduit 30 to a collection point 32. The collection point 32 is any sort of sample holder which is transparent to Raman spectroscopy, such as a glass tube.

Alternatively, the refrigeration means is a electrothermally controlled plate located in the path of the air sample. The plate is cooled below the freezing point of water. The air sample directly impinges on the plate and forms a frost on the surface of the plate a solid condensate consisting essentially of water and organic material. Using an electrothermally controlled plate incorporates the condensation area and collection point into one. The refrigerant and apparatus to be used depends on whether a liquid or solid sample is desired.

Analysis is by use of a Raman spectrometer 34 which utilizes a laser beam directed to the sample. The scatter of the laser beam after it impinges on the sample forms a spectra which is detected by any known means for detecting light 36, such as a photodetector. Certain chemical compositions have characteristic spectra which can be identified by comparison to a standard which can be done by a computer 38.

After analysis, the condensate is drained from the housing 10 by conduit 40. In the case of solid condensate, heat is applied by a heating element 42 to liquefy the solid condensate and facilitate its removal from the housing. For the electrothermally controlled plate the liquification is by means of a heat source within the plate. The uncondensed gases from the air sample also are exhausted by a conduit 44 from the housing.

Figure 3:
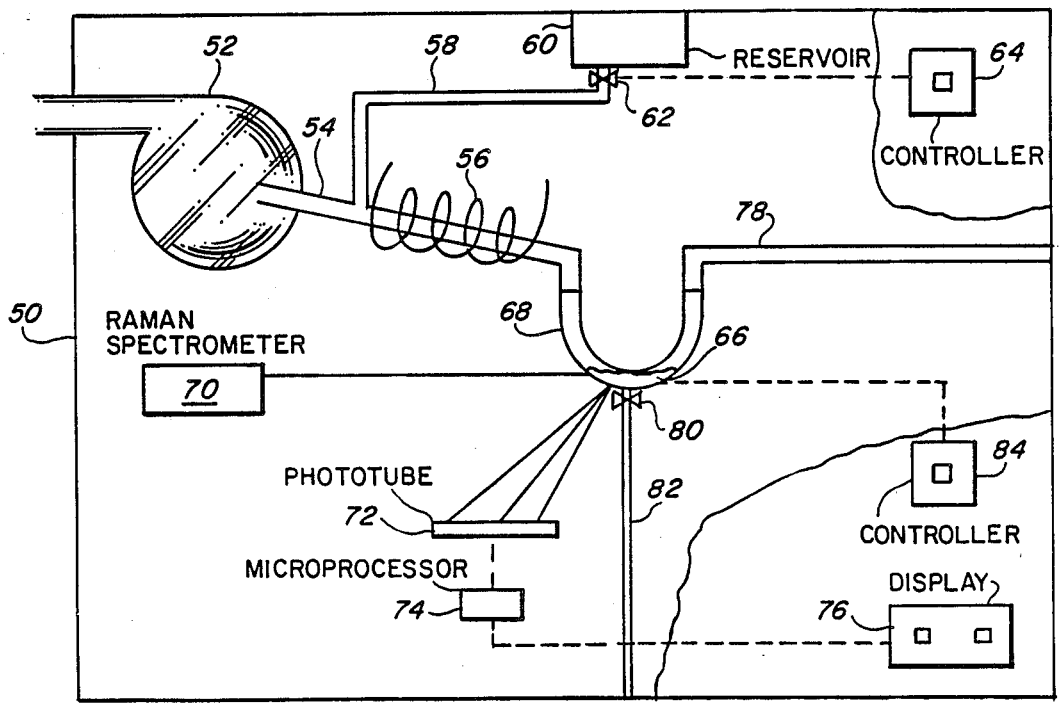
FIG. 3 is an illustration of one embodiment of the invention using a refrigeration coil to cool the air sample and a U-tube to collect the condensate.

Referring now to FIG. 3, which illustrates the preferred embodiment of the invention, a housing 50 contains an air pump 52 which draws air into in a continuous or noncontinuous manner as required. The air is pumped through a line 54 of material such as polytetrafluoroethylene, known under the trademark Teflon. The air is cooled by a refrigeration coil 56 around the line 54. The refrigeration coil 56 contains an appropriate commercially available refrigerant which cools the air to a temperature within the range of the cryogenic temperature of liquid air to 0° C., or within a preferred range of $-10°$ C. to $-5°$ C. or, most preferred, $-7°$ C. At these temperatures a condensate forms in the line 54. Distilled water is added through conduit 58 from reservoir 60. The flow of distilled water is controlled by a valve 62 which is activated by a controller 64 on the outside of the housing 50. The distilled water melts the solid condensate to form a solution 66 consisting essentially of water and organic material and is collected in a glass U-tube 68.

A miniaturized Raman spectrometer 70 constructed with laser diodes tuned to give desired analytical wavelengths subjects the condensate 66 to laser radiation. A phototube 72 detects the Raman spectra. The signal is compared to the signal for the spectra of the composition for which the analysis is being done by a microprocessor 74 which gives an output to a display 76 on the outside of the housing 50 such that it gives a positive or negative result.

The remaining uncondensed components of the air continue through the line 54 and tube 68 into the line 78 which exits the housing 50. After analysis of the condensate 66 is complete, it is removed by means of a valve 80 on a line 82 connected to the bottom of the tube 68. Activation of the valve 80 is by a control 84 on the outside of the housing 50. When the valve 80 is open the condensate flows through line 82 to the outside of housing 50.

Figure 4:
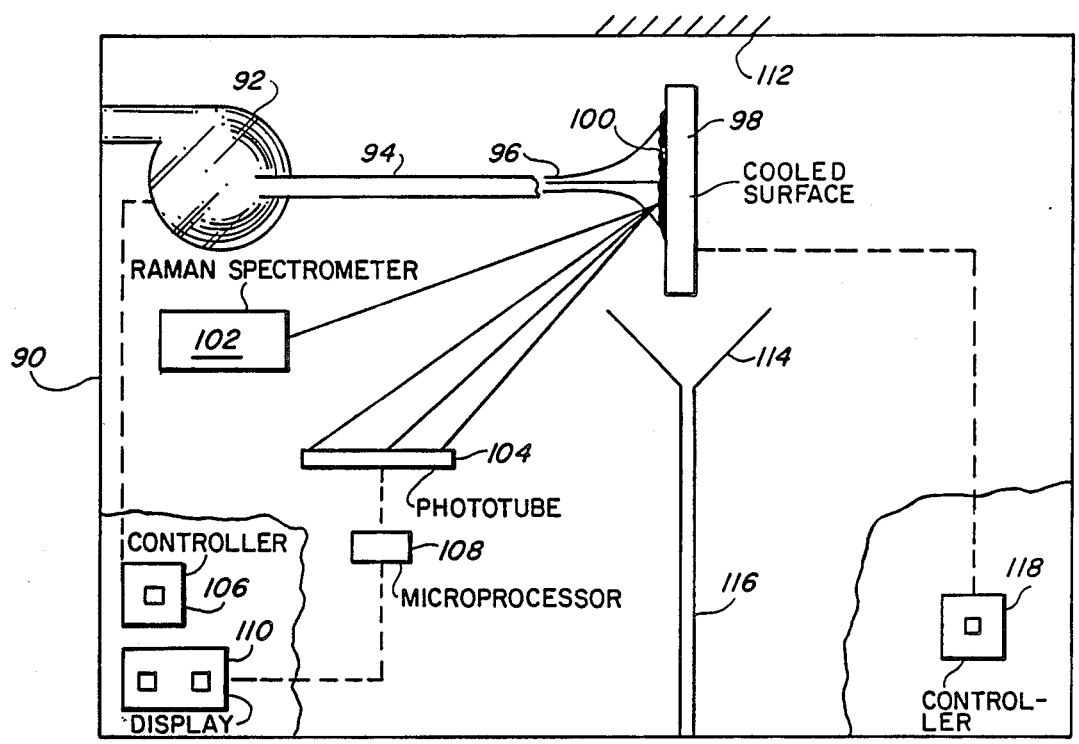
FIG. 4 is an illustration of alternative embodiment of the invention using a cooled surface to cool the air sample and form condensate as frost on its surface.

In an alternative illustration of the invention, FIG. 4 shows a housing 90 containing an air pump 92 which draws air in a controlled manner. The air is pumped through a line 94 to the end of the line 96 at which the air exits and impinges on a cooled surface 98 which would cool the air to a temperature within the range of above the cryogenic temperature of liquid air to 0° C., or within the preferred range of $-10°$ C. to $-5°$ C. or, most preferably, of exactly $-7°$ C.. At these temperatures frost 100 would deposit on the cooled surface.

A miniaturized Raman spectrometer 102 constructed with laser diodes tuned to give desired analytical wavelengths subjects the frost 100 to laser radiation. The reflected signal is detected by a phototube 104. During analysis by Raman spectroscopy, air flow into the housing will cease. The air pump 92 is deactivated by a control 106 on the outside of the housing 90.

Alternatively, the cooled surface 98 is concave so that the reflected signal could be more efficiently focused on the phototube 104. The signal is compared to the signal for spectra of the composition for which the analysis is being done by a microprocessor 108 which gives an output to a display 110 on the outside of the housing 90 such that it gives a positive or negative indication of the presence of the composition for which the analysis is being done.

The remaining uncondensed components of the air exit through an opening 112 in the top of the housing 90. After analysis of the frost 100 is complete, the cooled surface 98 is heated electrothermally so that the frost 100 liquefies and flows into a receptacle 114 which is connected to a line 116 that carries the liquified frost to the outside of the housing 90. Activation of the electrothermal heat is by a control 118 on the outside of the housing 90.

Figure 5:
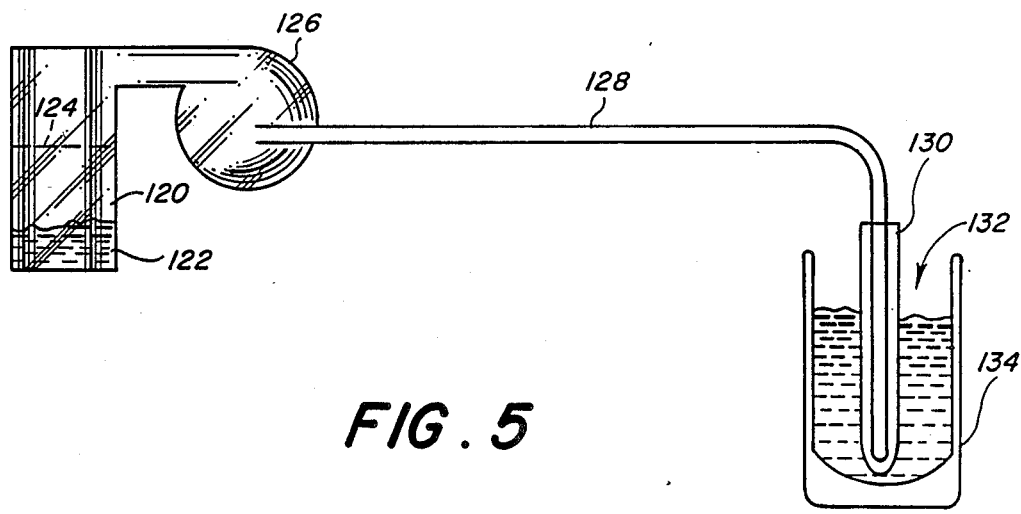
FIG. 5 is an illustration of the laboratory setup used to collect DMMP condensate.
Figure 6:
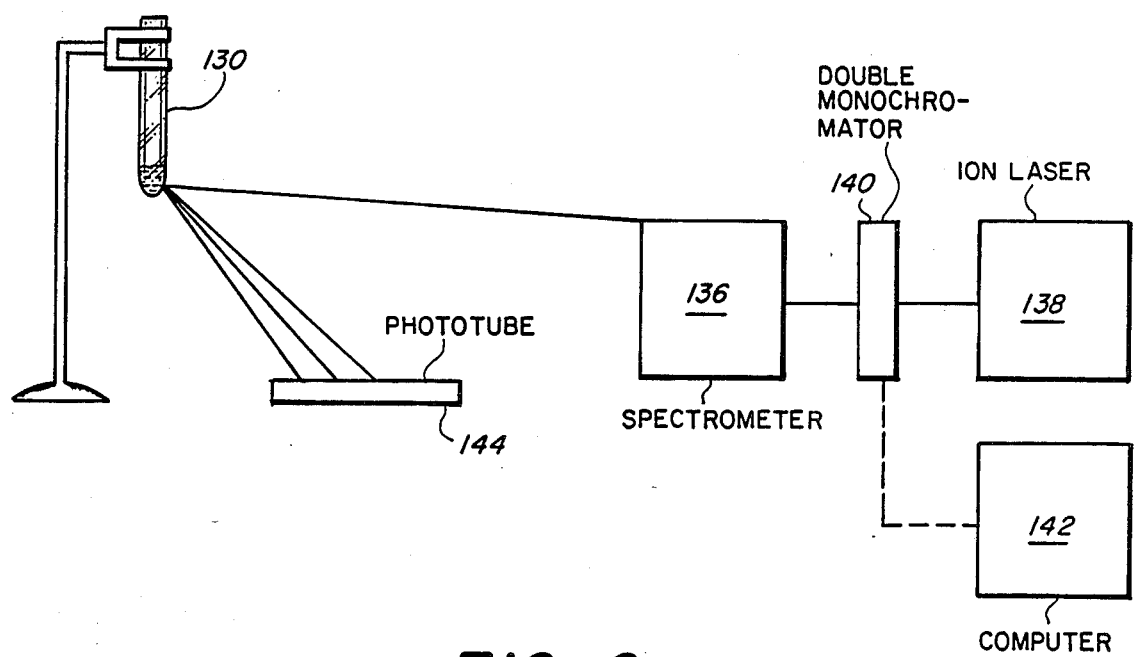
FIG. 6 is an illustration of the laboratory setup used to analyze the DMMP condensate.

To illustrate the basic elements of the invention, the following specific example of a laboratory procedure used to collect and analyze DMMP condensate is shown in FIGS. 5 and 6. It is recognized that the steps in this laboratory procedure requiring human handling or processing can b mechanized or automated to convert them into a commercially viable method and an apparatus for practicing that method. FIG. 5 illustrates the laboratory setup used to collect DMMP condensate. A calibrated permeation tube 120 containing DMMP liquid 122 allowed a known amount (20 micrograms/min) of DMMP vapor through a permeable membrane 124. The vapor was collected in a air stream by an air pump 126 and transported into a short length of ⅜" OD tubing of polyetrafluoroethylene, known under the trademark Teflon 128. The tubing 128 was held in a test tube 130 which was in a bath of dry ice and isopropanol 132 at −78° C. contained in a dewar vessel 134. After four hours of operation, 4.8 milligrams of DMMP condensate in the form of drops had collected on the walls of the tubing 128. The DMMP was flushed out of the tubing 128 with 1.0 milliliter of distilled water.

Figure 1:
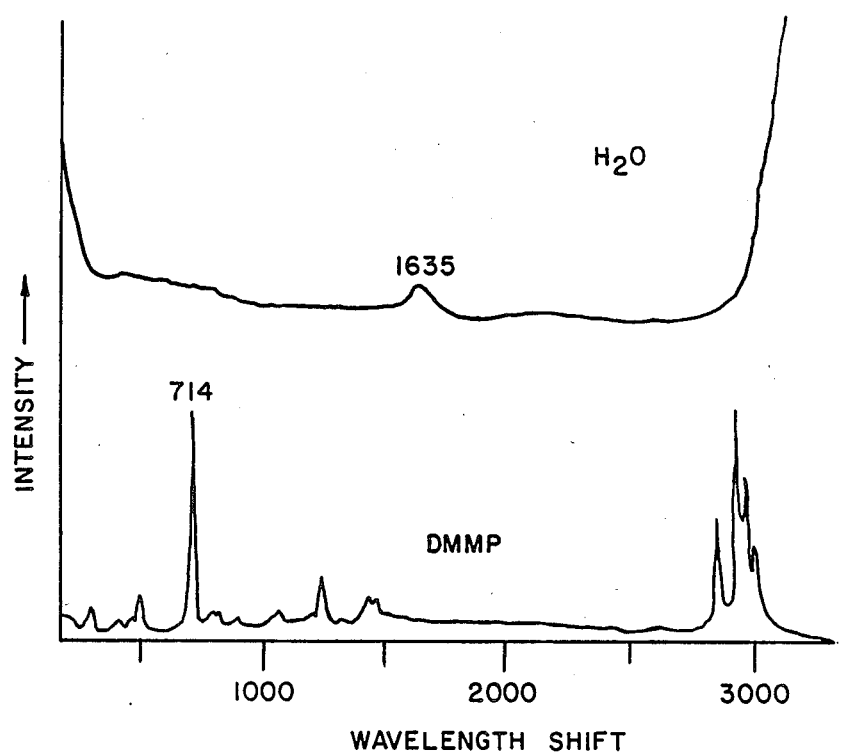
FIG. 1 is an illustration of Raman spectra for distilled water and dimethylmethylphosphonate.

FIG. 6 illustrates the laboratory setup used to analyze the DMMP condensate, the test tube 130 containing the collected condensate diluted with 1.0 milliliter of distilled water was subjected to laser radiation using a Jarrell-Ash model 500 Raman spectrometer 136 which excited the condensate with 50 milliwatts of power in the 488.0 and 514.5 lines of Spectra Physics model 164 argon ion laser 138. A double monochromator 140, computer controlled by a Commodore 64 computer 142, was used in conjunction with the laser excitation and signals were detected in the photon counting mode using a red-enhanced RCA 31034 phototube 144. Spectra were recorded graphically and measurement of peak intensity was made using the strongest lines present in the DMMP spectrum at 714 $cm^{-1}$. The 1635 $cm^{-1}$ line in water served as the internal standard as shown in FIG. 1.

The intensity of the 714 $cm^{-1}$ DMMP peak was calculated using the following procedure. The peak intensity and the background intensity at 714 $cm^{-1}$ and 1635 $cm^{-1}$, respectively, were measured. Next, the difference of peak intensity and background intensity at 714 $cm^{-1}$ was calculated. Similarly, the difference of peak intensity and background intensity at 1635 $cm^{-1}$ was calculated. Finally, a peak intensity ratio making the solvent peak the internal intensity standard for comparison among samples was calculated by dividing the difference of peak intensity and background intensity at 714 $cm^{-1}$ by the difference of peak intensity and background intensity at 1635 $cm^{-1}$. This normalized intensity was compared to a log-log graph of normalized intensity versus concentration (weight-weight ratio) for aqueous DMMP solutions.

Use of the above method and apparatus makes detection of 50–500 parts per billion of organophosphorus contaminants in air attainable. Use of a tunable ultraviolet laser excitation source and parallel detection with an optical multichannel analyzer could achieve increased sensitivity of 1–50 parts per billion.

The invention could be applied in situations where detection of low concentration of organic compounds is needed. In agriculture, the invention could be used to determine excess use of pesticides and herbicides. In industry, release of small amounts of a toxic or carcinogenic organic compound could be detected prior to an uncontrolled release due to a process upset. In the military, the invention could be used to detect chemical warfare agents and give an alarm before a life threatening situation occurred. The apparatus could be portable or permanently installed.

Obviously, numerous modifications and variations of the present invention are possible in light of the above teachings. It is therefore to be understood that within the scope of the appended claims, the invention may be practiced otherwise than as specifically described herein.

What is claimed and desired to be secured by Letters Patent of the United States is:

1. A method of detecting and quantifying an organic material in the atmosphere, comprising:
   a. collecting an air sample from the atmosphere;
   b. cooling the air sample to form a condensate consisting essentially of water and organic material from the air sample; and
   c. analyzing the condensate by Raman spectroscopy to detect and quantify the constituents in the organic material.

2. A method as recited in claim 1, wherein the air sample is collected with an air pump.

3. A method as recited in claim 1, wherein the sample is cooled to a temperature within a range from the cryogenic temperature of liquid air to 0° C. to condense the water and the organic material.

4. A method as recited in claim 3, wherein the sample is cooled to a temperature within a range from −10° C. to −5° C.

5. A method as recited in claim 4, wherein the sample is cooled to a temperature of −7° C.

6. A method as recited in claim 1, wherein the sample directly impinges upon an electrothermal device that cools the sample to form a solid condensate of organic material and water and, after analysis is complete, liquefies the solid for removal.

7. A method as recited in claim 1, wherein the air sample is cooled by flowing the sample through a tube around which is a refrigeration coil such that organic material and water is condensed in the tube.

8. A method as recited in claim 1, wherein analyzing the condensate is done with a Raman spectrometer having a laser diode tuned to a predetermined wavelength for a particular component being detected.

9. An apparatus to detect and quantify organic material in air, comprising:
   a. a housing having an opening for collecting an air sample;
   b. a collecting means connected to the opening in the housing which collects the air sample and moves it into and through the apparatus;
   c. a cooling means positioned to cool the air sample collected by the collecting means such that a condensate consisting essentially of organic material and water is formed;
   d. a condensate collecting means positioned to collect the organic material and water condensed by the cooling means;
   e. an analyzing means positioned to analyze the organic material in the collected condensate by Raman spectroscopy; and f. exhaust means positioned to exhaust from the housing the uncondensed gases from the collecting means and the condensate from the condensate collecting means.

10. An apparatus as recited in claim 9, wherein the means for collecting an air sample comprises:
   a. a flow-controlling valve;
   b. a conduit which is connected to the flow-controlling valve; and
   c. an air pump connected to the conduit for moving the air sample from the opening in the housing into and through the apparatus.

11. An apparatus as recited in claim 10, wherein the cooling means is capable of cooling the air sample to a temperature in the range from the cryogenic temperature of liquid air to 0° C.

12. An apparatus as recited in claim 10, wherein the cooling means is capable of cooling the air sample to a temperature in the range from $-10°$ C. to $-5°$ C.

13. An apparatus as recited in claim 10, wherein the cooling means is capable of cooling the air sample to a temperature of $-7°$ C.

14. An apparatus as recited in claim 13, wherein the means for analyzing condensate is a Raman spectrometer with laser diodes tuned to the wavelengths of the component for which analysis is desired.

15. An apparatus as recited in claim 14, wherein the means for analyzing condensate is a Raman spectrometer with a tunable ultraviolet laser excitation source.

16. An apparatus as recited in claim 15, wherein the means for analyzing condensate is a Raman spectrometer with parallel detection by an optical multichannel analyzer.

17. An apparatus as recited in claim 16, wherein the means for cooling the air sample is an electrothermal device that cools the air sample until a solid condensate is formed and, after the analysis is complete, heats the slid condensate until it liquefies.

18. An apparatus as recited in claim 17, wherein the means for collecting the condensate is the surface of the electrothermal device upon which the solid condensate forms.

19. An apparatus as recited in claim 18, wherein the electrothermal device has a concave surface which focuses the scattered light from a Raman spectrometer source on a detector.

20. An apparatus as recited in claim 16, wherein the means for cooling the air sample is a conduit through which the air sample flows and around which a refrigeration coil is placed so that condensate forms in the conduit.

21. An apparatus as recited in claim 20, wherein the means for collecting the condensate is a glass U-tube connected to the conduit so that the condensate flows into the glass U-tube.

* * * * *